US009086414B2

(12) United States Patent
Petricoin, III et al.

(10) Patent No.: US 9,086,414 B2
(45) Date of Patent: Jul. 21, 2015

(54) PHOSPHORYLATED C-ERBB2 AS A SUPERIOR PREDICTIVE THERANOSTIC MARKER FOR THE DIAGNOSIS AND TREATMENT OF CANCER

(75) Inventors: Emanuel F. Petricoin, III, Gainesville, VA (US); Lance A. Liotta, Bethesda, MD (US); Virginia Espina, Rockville, MD (US); Julia D. Wulfkuhle, Columbia, MD (US)

(73) Assignee: George Mason Research Foundation, Inc., Fairfax, VA (US)

( * ) Notice: Subject to any disclaimer, the term of this patent is extended or adjusted under 35 U.S.C. 154(b) by 969 days.

(21) Appl. No.: 13/003,206

(22) PCT Filed: Jul. 8, 2009

(86) PCT No.: PCT/US2009/049903
§ 371 (c)(1),
(2), (4) Date: Apr. 14, 2011

(87) PCT Pub. No.: WO2010/006027
PCT Pub. Date: Jan. 14, 2010

(65) Prior Publication Data
US 2011/0189173 A1    Aug. 4, 2011

Related U.S. Application Data

(60) Provisional application No. 61/078,956, filed on Jul. 8, 2008.

(51) Int. Cl.
*A61K 39/395*  (2006.01)
*A01N 43/48*  (2006.01)
*G01N 33/53*  (2006.01)
*G01N 33/543*  (2006.01)
*G01N 33/574*  (2006.01)
*C12Q 1/68*  (2006.01)
*A61K 31/517*  (2006.01)
*G01N 1/30*  (2006.01)
*A61K 39/00*  (2006.01)

(52) U.S. Cl.
CPC ........ *G01N 33/57492* (2013.01); *A61K 31/517* (2013.01); *A61K 39/39558* (2013.01); *C12Q 1/6841* (2013.01); *C12Q 1/6886* (2013.01); *G01N 1/30* (2013.01); *G01N 33/54366* (2013.01); *G01N 33/574* (2013.01); *G01N 33/57415* (2013.01); *A61K 2039/505* (2013.01); *C12Q 2600/106* (2013.01); *C12Q 2600/112* (2013.01); *G01N 2033/57403* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| 2006/0204966 A1 | 9/2006 | Spector et al. |
| 2007/0254295 A1 | 11/2007 | Harvey et al. |
| 2008/0255243 A1 | 10/2008 | Petricoin et al. |
| 2009/0148859 A1 | 6/2009 | Liotta et al. |
| 2010/0003247 A1 | 1/2010 | Petricoin et al. |
| 2010/0074895 A1 | 3/2010 | Petricoin et al. |
| 2010/0317740 A1 | 12/2010 | Petricoin et al. |
| 2011/0200597 A1 | 8/2011 | Petricoin et al. |

FOREIGN PATENT DOCUMENTS

| WO | WO 2004/008099 A2 | 1/2004 |
| WO | WO 2005/011607 A2 | 2/2005 |
| WO | WO 2006/063042 A2 | 6/2006 |
| WO | WO 2006/091693 A2 | 8/2006 |
| WO | WO2007041502 * | 4/2007 |
| WO | WO 2007/106432 A2 | 9/2007 |
| WO | WO 2010/028313 A2 | 3/2010 |

OTHER PUBLICATIONS

Ouyang et al (Molecular and Cellular Biochemistry, 2001, vol. 218, pp. 47-54).*
Cicenas et al (European Journal of Cancer, 2006, vol. 42, pp. 636-645).*
Hudelist et al (British Journal of Cancer, 2003, vol. 89, pp. 983-991).*
Guo et al (International Journal of Biological Markers, 2007, vol. 22, pp. 1-11).*
Cowherd et al (Clinical Breast Cancer, 2004, vol. 5, pp. 385-392).*
The abstract of Paik et al (Journal of Clinical Oncology, 2007, vol. 25, No. 18S, (Jun. 20, supplement), p. 511).*
Koeppen et al (Histopathology, 2001, vol. 38, pp. 96-104).*
V. Espina, et al., "Pathology of the Future: Molecular Profiling for Targeted Therapy," Cancer Investigation, 1:36-46, 2005.

(Continued)

*Primary Examiner* — Karen Canella
(74) *Attorney, Agent, or Firm* — Geoffrey M. Karny

(57) ABSTRACT

The present invention provides reliable methods to identify subsets of subjects with a cancer of epithelial origin characterized by a high level of phosphorylated c-erbB2 which does not correlate with the over-expression of total c-erbB2 as measured by IHC or FISH, for selection and inclusion for c-erbB2-direct treatment and therapy. Furthermore, the present invention provides a reliable method to determine whether a subject with a cancer of epithelial origin who has been determined to be c-erbB2 positive by IHC and by FISH should be excluded from c-erbB2-direct treatment because of a non-significant level of phosphorylated c-erbB2 in epithelial tumor tissue.

49 Claims, 9 Drawing Sheets

(56) References Cited

OTHER PUBLICATIONS

A. Vanmeter, et al., "Laser Capture Microdissection and Protein Microarray Analysis of Human Non-small Cell Lung Cancer," Molecular and Cellular Proteomics 7.10. ASBMB, pp. 1902-1924, 2009.

J. Wulfkuhle, et al., "Genomic and proteomic technologies for individualisation and improvement of cancer treatment" European Journal of Cancer 40 (2004) 2623-2632.

International Search Report and Written Opinion of the European Patent Office on International App.No. PCT/US2009/049903 of George Mason Intellectual Properties, Inc., Oct. 12, 2009.

* cited by examiner

PHOSPHORYLATED C-ERBB2 AS A SUPERIOR PREDICTIVE THERANOSTIC MARKER FOR THE DIAGNOSIS AND TREATMENT OF CANCER

CROSS REFERENCE TO RELATED APPLICATIONS

This application is a U.S. national phase application of, and claims priority to and the benefit of, International Patent Application No. PCT/US2009/049903, filed Jul. 8, 2009, which claims priority to and the benefit of, U.S. Provisional Patent Application No. 61/078,956, filed Jul. 8, 2008. The disclosures of these applications are expressly incorporated herein by reference in their entireties.

BACKGROUND OF THE INVENTION

The human epidermal growth factor receptor-2 (HER2/neu; erbB2) oncogene encodes a transmembrane tyrosine kinase receptor with extensive homology to the epidermal growth factor receptor (EGFR). erbB2 belongs to a family of four transmembrane receptor tyrosine kinases involved in signal transduction pathways that regulate cell growth and proliferation in tissues of epithelial, mesenchymal and neuronal origin. Ligand binding to erbB2 receptors results in dimerization, including heterodimerization with other EGFR family members such as c-erbB3 and EGFR, and kinase activation, followed by phosphorylation of tyrosine residues in the intracellular receptor cytoplasmic tail. Phosphorylated tyrosines provide recognition sites for intracellular signaling intermediates that provide the link to downstream transduction cascades. Amplification or over-expression of erbB2 leads to transformation in the absence of a ligand through enhanced cell proliferation, motility and adhesion.

Clinical studies indicate that c-erbB2/HER2 is overexpressed in certain types of tumors of epithelial origin. Cancers that originate from epithelial cells, including those of the breast, lung, prostate, ovary, stomach, pancreas, bladder, rectum, colon, kidney, head and neck, as well as glioblastoma and adenocarcinoma, are by far the most common types of cancer in adults. Over-expression of erbB2 is present in about 30% of invasive human breast and ovarian cancers and is associated with a poor clinical outcome, including short survival time and short time to relapse. Similarly, c-erbB2 gene amplification or over-expression has been reported in ovarian cancer. c-erbB2 is also amplified and/or over-expressed in both benign and malignant prostate tissue, where c-erbB2 over-expression is associated with large tumor volume, high tumor grade and distant metastases, as well as in 50% of invasive bladder cancers. Development of adenocarcinoma in the esophagus and cancer of the stomach have also been associated with over-expression of the c-erbB2.

Because of the prognostic and predictive value of c-erbB2, the status of c-erbB2 is routinely tested in invasive cancers. Methodologies to identify over-expression of HER2 include immunohistochemistry (IHC); silver, chromogenic, or fluorescent in situ hybridization (SISH/CISH/FISH); and PCR-based technologies.

HER-2 protein over-expression is routinely determined by IHC. Highly standardized, semi-quantitative IHC assays and scoring procedures have been developed which categorize HER2 expression levels in a scale from 0 to 3+, with 0 being lack of protein expression and 3+ corresponding to cells containing approximately 2,300,000 receptors/cell, showing HER2 over-expression in more than 10% of the cells. Advantages of IHC testing include its wide availability, relatively low cost, easy preservation of stained slides, and use of a familiar routine microscope. Disadvantages include the impact of pre-analytic issues, including, for example, storage, duration and type of fixation, type of antibody, nature of system control samples, and, importantly, the difficulties in applying a subjective slide scoring system. Fluorescent in-situ hybridization (FISH) determines the level of c-erbB2 over-expression in patients, by detecting gene amplification. This technique is expensive and requires a fluorescent microscope and image captures system. Currently, the recommended assays most commonly used for determining the c-erbB2/HER2 status of breast cancer tissue are a combination of IHC and FISH, where tissue samples receiving IHC scores of 0 and 1+ are considered negative for HER2 over-expression, and those receiving scores of 3+ are positive for HER2 over-expression. Tissue samples receiving scores of 2+ and 2+/3+ are reexamined using FISH for a final determination.

HER2/neu over-expression is often used to predict which cancer patients are most likely to benefit from certain cancer treatments that directly bind with the HER2/neu protein and modulate its biological activity via a number of mechanisms. Thus, trastuzumab, which is marketed under the tradename HERCEPTIN® by Genentech Corporation, South San Francisco, Calif., is an FDA-approved drug for use in HER2-positive metastatic breast cancer in combination with paclitaxel as a first-line therapy, and as a single agent in second- and third-line therapy for metastatic breast cancer patients after other therapies have failed. HERCEPTIN® has also been approved by the FDA for the adjuvant treatment of patients with HER-2 positive node-positive breast cancer as part of a treatment regimen containing doxorubicin, cyclophosphamide and paclitaxel, and as a single agent for the adjuvant treatment of HER-2 over-expressing node-negative or node-positive breast cancer, following multi-modality anthracycline-based therapy. Trastuzumab is a humanized mouse monoclonal antibody that specifically binds the C-terminal end of domain IV of the extracellular region of the HER2/neu receptor. Cells treated with trastuzumab undergo arrest during the G1 phase of the cell cycle, leading to a reduction in cell proliferation. Trastuzumab is believed to induce some of its effects by down-regulating HER2/neu, leading to the disruption of receptor dimerization and cell signaling through downstream signaling cascades.

Trastuzumab therapy was initially targeted specifically for patients with advanced relapsed breast cancer that over-expressed the HER2/neu protein. Currently, initiation of trastuzumab therapy is based upon the identification of HER2/neu over-expression in the breast tumor tissue of a patient, under the assumption that those patients most likely to respond to trastuzumab therapy are those having breast cancer that over-expresses HER2/neu+ ("HER2/neu+ patients").

Lapatinib, marketed by GlaxoSmithKline (GSK) under the trade names TYKERB® and TYVERB®, is an ATP-competitive epidermal growth factor receptor (EGFR) and HER2/neu (ErbB-2) dual tyrosine kinase inhibitor, that inhibits receptor auto-phosphorylation and activation by binding to the ATP-binding pocket of the EGFR/HER2 protein kinase domain. Lapatinib has shown remarkable activity both in vitro and in vivo, leading to growth arrest and apoptosis of tumor cell lines that over-express EGFR or HER2 in a variety of tumors, including breast and renal cancers. Lapatinib is approved by the FDA for use in patients with advanced metastatic breast cancer in conjunction with the chemotherapy drug capecitabine and is indicated for patients with resistance to trastuzumab.

In view of the utility of HER2 as a predictive marker, the American Society of Clinical Oncology and the College of American Pathologists convened an expert panel that developed recommendations for optimal HER2 testing performance and recommended that HER2 status should be determined for all invasive breast cancer.

Despite the commonly-accepted expectation that HER2 amplification in cancer patients predicts benefit from trastuzumab therapy for these patients, a recent publication from Paik et al. (NEJM, Mar. 27, 2008), found no significant association between HER2 gene copy number and patient benefit, and provided strong evidence that approximately 10% of the HER2-negative patients studied in a large cohort of a National Surgical Adjuvant Breast and Bowel Project (NSABP) trial responded to and benefited from trastuzumab therapy. Moreover, therapeutic success, as defined by statistical significance in overall survival, or progression free survival or time to progression, for breast cancer patients with high expression of c-erbB2 (e.g. FISH+ and/or IHC 3+) is only approximately 50%. In other words, half of the patients with high expressing HER2 protein do not respond to HER2-directed therapy and about 10% of HER2-patients respond to therapy despite having low levels of the protein expressed.

Accordingly, there is an urgent need in the art to develop a more reliable and accurate method(s) to identify subjects with a cancer of epithelial origin who would respond to and benefit from trastuzumab therapy or treatment with a c-erbB2 kinase inhibitor, for selection and inclusion for erbB2-directed treatment and therapy. The present invention satisfies this need.

SUMMARY OF THE INVENTION

It is therefore an object of the invention to provide solutions to the aforementioned deficiencies in the art.

It is an object of the present invention to provide a method to determine selection and inclusion for erbB2-directed treatment and therapy of a subject with a cancer of epithelial origin who has been determined to be c-erbB2 negative by immunohistochemistry (IHC) and by fluorescence in situ hybridization (FISH). The subject may belong to a population cohort that would otherwise not receive this therapy.

It is a further object of the invention to provide a method to identify a subject with a cancer of epithelial origin who would benefit from treatment with an EGF receptor dimerization inhibitor, trastuzumab or an analogue compound thereof, or a c-erbB2 kinase inhibitor.

It is yet another object of the present invention to provide a method to determine a priori a poor or a good prognosis for a subject with a cancer of epithelial origin.

It is still another object of the invention to provide a method to determine the level of phosphorylation of the c-erbB2 receptor in a subject with a cancer of epithelial origin.

It is another object of the invention to provide a method to determine whether a subject with cancer of epithelial origin who has been determined to be c-erbB2 positive by immunohistochemistry (IHC) and by fluorescence in situ hybridization (FISH) should be excluded from treatment with an EGF dimerization inhibitor, trastuzumab or an analogue compound thereof, or a c-erbB2 kinase inhibitor, thus saving unnecessary expense, potential cardiotoxicity side-effects associated with trastuzumab therapy without clinical benefit, and triage into other treatment trials.

To accomplish these and other objectives, the invention provides methods comprising measuring the level of phosphorylation of the c-erbB2 receptor in one or more diseased cells obtained from the cancerous epithelial tissue of the subject and comparing the level of phosphorylation in the diseased cells to the level of phosphorylation of reference standards.

In one aspect of the invention, a c-erbB2 phosphorylation level greater than the cut-point value obtained from a reference standard that is printed concomitantly with the subject sample indicates that the subject should be considered for inclusion into erbB2-directed treatment and therapy. The cut-point is obtained by comparing a population average level of phosphorylation of known erbB2-phosphorylated cancers to the level of phosphorylation of reference lysates from cell lines with high levels of c-erbB2 and phosphorylated c-erbB2 and cell lines with low levels of c-erbB2 and phosphorylated c-erbB2.

In another aspect of the invention, a phosphorylation level greater than the cut-point indicates that the subject would benefit from treatment with an EGF receptor dimerization inhibitor, trastuzumab or an analogue compound thereof, or a c-erbB2 kinase inhibitor.

In yet another aspect of the invention, a phosphorylation level greater than the cut-point indicates a poor prognosis for the subject.

In another aspect of the invention, a phosphorylation level greater than the cut-point indicates a high level of phosphorylated c-erbB2 receptor.

In still another aspect of the invention, a phosphorylation level smaller than the cut-point indicates that the subject should be excluded from treatment with an EGF receptor dimerization inhibitor, trastuzumab or an analogue compound thereof, or a c-erbB2 kinase inhibitor.

In one aspect of the invention, the diseased cells are tumor cells micro-dissected from tissue/biopsy specimens by laser capture micro-dissection. In one embodiment, the level of phosphorylation of the c-erbB2 receptor in the diseased cells is measured by protein microarray analysis. In a preferred embodiment, the protein microarray analysis is reverse phase protein microarray analysis. In a further embodiment, measuring the level of phosphorylation of the c-erbB2 receptor in the diseased cells comprises the use of antibodies that specifically bind to phosphorylated c-erbB2 receptor. In a preferred embodiment, the antibodies are monoclonal antibodies.

In a specific embodiment, the reference standards are a series of lysates derived from the breast cancer cell line SKBR3 and the carcinoma cell line MDA175. In a preferred embodiment, prior to lysis, the cells are stimulated with EGF producing a reference standard with high (SKBR3) and low (MDA175) amounts of phosphorylated c-erbB2. In a different embodiment, the reference standards are a series of lysates derived from a c-erbB2-negative cell line spiked with recombinant or partially purified phosphorylated c-erbB2, or spiked with phosphorylated c-erbB2 peptide at a series of known concentrations of phosphorylated c-erbB2.

In one aspect of the invention, the subject or patient has a cancer of epithelial origin. In a preferred embodiment, the subject or patient suffers from glioblastoma, adenocarcinoma, or a cancer of the breast, prostate, lung, ovary, stomach, pancreas, bladder, colon, rectum, kidney, liver, head, neck or any combination thereof.

In another aspect of the invention, the subject or patient has a cancer of epithelial origin that has metastasized to at least one organ site that is distinct from the originating organ. In a preferred embodiment, the subject or patient suffers from metastatic lesions within the liver, lung, brain, bone, peritoneal cavity, lymphatic system, skin, or other highly vascularized organs.

In some aspects, the methods of the invention may further comprise treating a subject or a patient with a high level of phosphorylation of the c-erbB2 receptor with trastuzumab or an analogue compound thereof. In one embodiment, treatment with trastuzumab or an analogue compound thereof is adjuvant therapy, and the subject or patient is being treated with paclitaxel, doxorubicin, cyclophosphamide, a COX-2 inhibitor, a non-voltage gated calcium influx channel effector or an EGF kinase inhibitor. In other aspects, the methods of the invention may further comprise treating a subject or a patient with a high level of phosphorylation of the c-erbB2 receptor with a c-erbB2 kinase inhibitor. In a preferred embodiment, the c-erbB2 kinase inhibitor is lapatinib or an analogue compound thereof and the subject or patient is being treated with capecitabine.

In other aspects, the methods of the invention may further comprise excluding a subject or a patient with a low level of phosphorylation of the c-erbB2 receptor from treatment with trastuzumab or an analogue compound thereof, or a c-erbB2 kinase inhibitor.

DETAILED DESCRIPTION OF THE INVENTION

Figure 1:
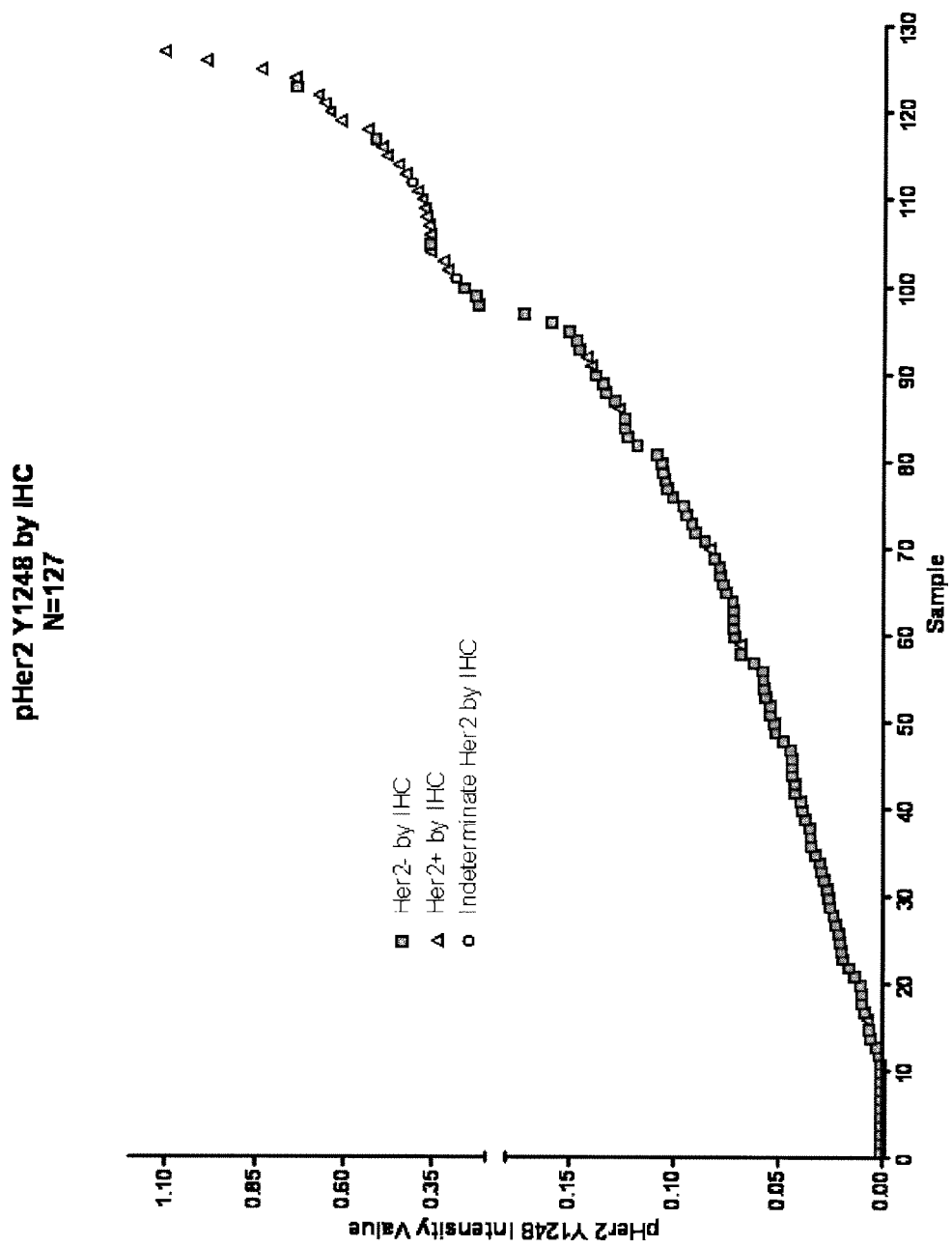
FIG. 1 presents a graph comparing the phosphorylation level of c-erbB2 of laser capture micro-dissected breast tumor epithelium as measured by reverse phase protein microarray analysis (RPMA) (relative expression of phosphorylated c-erbB2 is shown on the y-axis). The RPMA values are expressed in relative intensity units. The black squares represent a subpopulation of HER2-negative subjects with a negative IHC staining of 1+; the grey circles represent a subpopulation of subjects with an intermediate IHC staining of 2+; and the grey triangles represent a subpopulation of HER2-positive subjects with a positive IHC staining of 3+. The x-axis refers to the sample number, which are arranged in order of relative intensity of phosphorylated c-erbB2 staining.

The present invention provides methods to identify subpopulations of subjects with a cancer of epithelial origin who would respond and benefit from erbB2-directed treatment and therapy. The present methods rely on the measurement of the "activation" or "phosphorylation" status of c-erbB2 receptor in tumor tissue of a subject with a cancer of epithelial origin. The methods of the present invention are reliable and more accurate predictor of a subject's response to erbB2-directed treatment and therapy than the measurement by IHC and FISH of total c-erbB2 and c-erbB2 amplification in tumor tissue, respectively.

The terms "subject" and "patient" are used interchangeably, and are meant to refer to any mammal, including humans, that has, or is at risk of developing, a cancer of epithelial origin. The subject or patient is typically human, however, other suitable subjects or patients include, but are not limited to, laboratory animals, such as mouse, rat, rabbit, or guinea pig, farm animals and domestic animals or pets. Non-human primates are also included. The present methods can be used at any stage of epithelial cancer. For example, the methods can be used with subjects having early stage cancer; subjects having late-stage cancer and subjects in remittance from cancer, including recurring cancer; and subjects having active cancer, including active recurring cancer.

Diseased tumor cells are typically obtained from cancerous tissue samples and can be excised from the tissue using any suitable method in the art. In particular, diseased cells may be micro-dissected using laser-capture micro-dissection techniques.

The term "c-erbB2" is used interchangeably with HER2. The term "phospho-cerb2" is interchangeable with "pcerbB2", "phosphoHER2" and "pHER2" and the like and refers to the phosphorylated form of the protein. The term "FISH+/IHC+ HER2" refers to samples that are positive for HER2 as measured by fluorescent in situ hybridization and/or immunohistochemistry. Such methods typically measure the overexpression of HER2 in a sample, whereas methods for measuring the phosphorylated state of HER2 indicate the activation status of HER2/c-erbB2.

The phrase "activation status of c-erbB2 protein" refers to the level of phosphorylated c-erbB2 in the diseased tumor cells compared to reference standards. "Activated c-erbB2" refers to an isoform of c-erbB2 present in the cell that functions in a cell signaling pathway. Isoforms are typically post-translationally modified forms of c-erbB2, including, for example, forms of c-erbB2 that are phosphorylated, myristoylated or glycosylated.

The term "cut-point" refers to the value obtained by comparing a population average level of phosphorylation of known erbB2-phosphorylated cancers to the level of phosphorylation of reference lysate standards from cell lines with high levels of erbB2 and phosphorylated c-erbB2.

A cut-point is determined by statistical analysis of the population distribution using a statistical method such as a receiver operating characteristic (ROC) curve to define and obtain an optimal intensity value of an analyte, such as phosphorylated c-erbB2, that best discriminates two populations from each other. The ROC method is a graphical plot of the sensitivity vs. (1−specificity) for a binary classifier system as its discrimination threshold is varied. See, e.g., Cleophas et al. *Curr. Clin. Pharmacol.* (2008) 3:70-76, which is hereby incorporated by reference.

Figure 2:
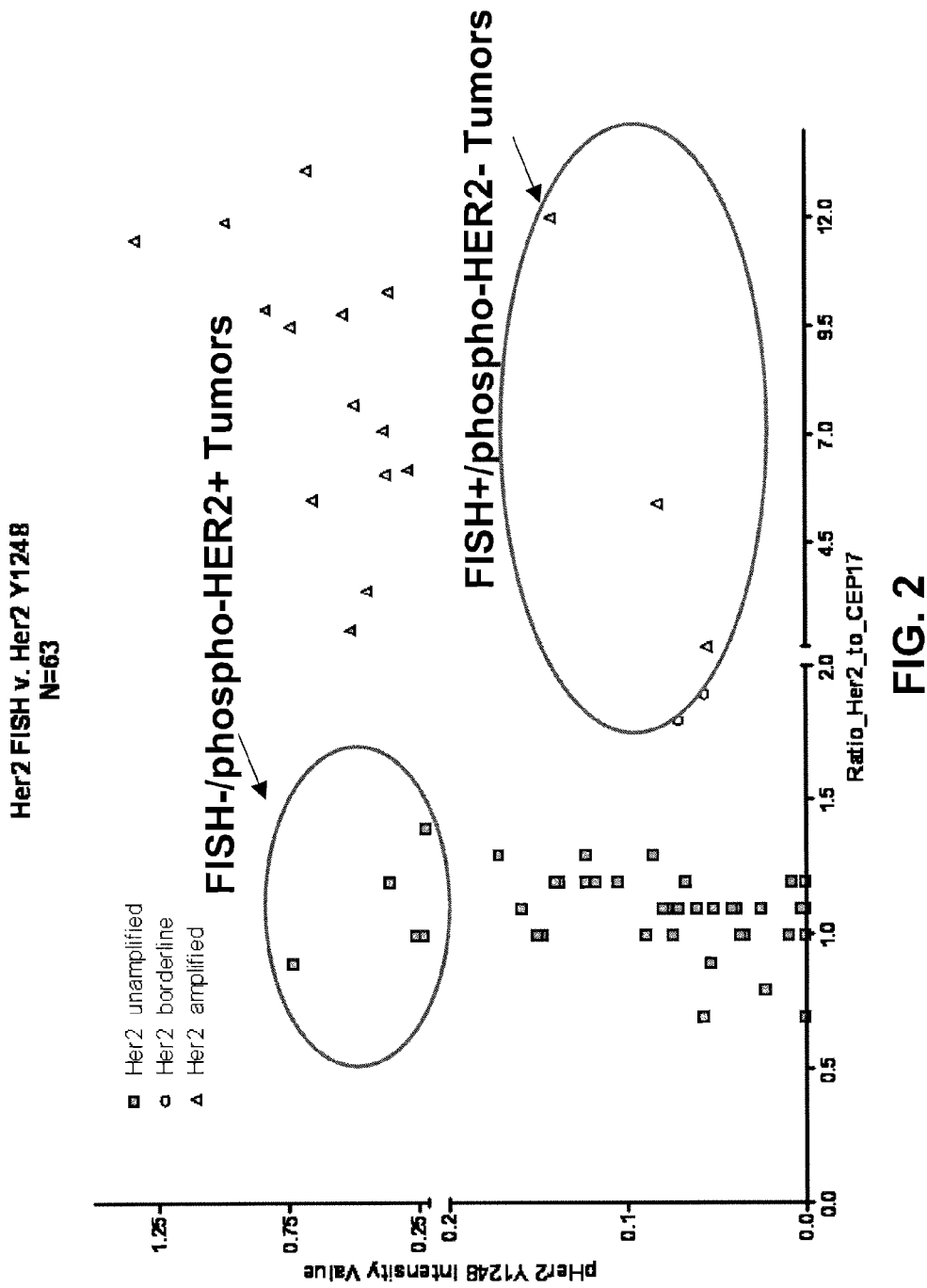
FIG. 2 presents a graph comparing the phosphorylation level of c-erbB2 of laser capture micro-dissected breast tumor epithelium as measured by reverse phase protein microarray analysis (RPMA) (y-axis) to the total level of c-erbB2 as measured by FISH (x-axis). RPMA values are expressed in relative intensity units. The black squares represent a subpopulation of HER2-negative subjects with a negative FISH staining (<1.5) the grey circles represent a subpopulation of subjects with an intermediate FISH result (1.5-2.0) and the grey triangles represent a subpopulation of HER2-positive subjects with a positive FISH result (>2.0). The bottom right circle indicates measurements in cancerous epithelial tissue micro-dissected from 3 subjects (3 of 17, 17% FISH+) that were determined both by IHC and FISH to be HER2-positive, but resulted phospho-c-erbB2-negative by RPMA and presented the same level of phosphorylated c-erbB2 presented by the majority of the HER2-negative subjects (17% of the HER2-positive population). The top left circle indicates a subpopulation of five HER2-negative, phospho HER2-positive subjects (11% of the HER2-negative population).

For example, in the data presented in FIG. 2, ROC analysis produces an optimal cutpoint of 0.22 relative intensity units, with a 74% sensitivity and 95% specificity for FISH− vs FISH+ tumors. This cut-point, derived from the input population data, reveals 5 patients who are FISH− yet have phosphorylated HER2 levels that have the same median and range as the FISH+ population above the 0.22 value. Translation of this cut-point to a reference standard is made possible by printing lysates of well-characterized cell lines that are known to have high or low levels of c-erbB2 and its phosphorylated state, with the same samples that comprise the population data. For example, in the data presented herein, a lysate produced from SKBR3 cells, known to highly over-express c-erbB2, is printed on the same RPMA as the experimental samples that comprise the population data. The 0.22 cut-point value is translated to the intensity value of the SKBR3 lysate, after normalization to total protein, by normalization to the SKBR3 value obtained on the same assay. Consequently, this value can be used prospectively in further assays whereby the SKBR3 lysate is used as a "bridging" case, printed on every subsequent array assay along with new patient samples, and obtained phospho-cerbB2 values can be compared to the SKBR3 value. Relative intensity values from each incoming new patient that are above the pre-determined cut-point value, now normalized to SKBR3, are defined as phospho-erbB2+, whereas patient samples that generate normalized intensity values below the cut-point are defined as phospho-erbB2−.

"Reference standards" refer to cells or lysates from cell lines or tumors with known characteristics, such as a known phosphorylation level or HER2 gene copy number. For example, lysates derived from the breast cancer cell line SKBR3 and the carcinoma cell line MDA175 can be used as reference standards and are recognized as such by the Food and Drug Administration as such. These cells, prior to lysis, are stimulated with EGF producing a reference standard with high (SKBR3) and low (MDA175) amounts of phosphorylated c-erbB2. "Reference standards" may also refer to a series of lysates derived from a c-erbB2-negative cell line spiked with recombinant or partially purified phosphorylated c-erbB2, or spiked with phosphorylated c-erbB2 peptide at a series of known concentrations of phosphorylated c-erbB2.

Any assay system that can quantify levels of the phosphorylated/activated forms of a protein can be used to measure the level of phosphorylated c-erbB2 in diseased tumor cells in the methods of the invention. In a preferred embodiment, the level of phosphorylation of the c-erbB2 receptor in the diseased cells is measured by protein microarray analysis. In an even more preferred embodiment, the protein microarray analysis is reverse phase protein microarray analysis. See, for example, Liotta et al., *Cancer Cell.* 3(4): 317-25 (2003), Paweletz et al., *Oncogene* 20(16): 1981-9 (2001).

Briefly, a protein microarray is an assay format that utilizes a substrate for simultaneously testing multiple samples. The microarray format is not limited to particular embodiments, but can comprise any arrangement and substrate that serves to provide a plurality of individual samples for testing. For example, in some embodiments, the microarray comprises a flat substrate with rows and columns of individual spots, each spot comprising a sample, while in other embodiments, the microarray comprises a flat substrate with a plurality of depressions, for example, a 96-well plate, in which each depression contains one sample. Examples of typical microarray substrates include nitrocellulose, derivatized glass slides, and 3-dimensional substrates such as hydrogels. Examples of nitrocellulose-coated glass slides include FAST slides (Schleicher & Schuell BioSciences, Keene, N.H.), which have protein binding capacities of 75-150 ug/cm$^2$ in a volume of 0.3-2.0 nl/spot. Nitrocellulose-coated glass slides are particularly useful, as a variety of detection methods can be used with this substrate, including chromogenic, fluorometric and luminescent detection methods.

The number of samples that can be deposited onto a microarray substrate can vary. The size of the substrate can often determine how many samples are located on the substrate. In some embodiments, the protein microarray comprises around 100 spots; in other embodiments, the protein microarray may comprise around 1,000 spots or around 10,000 spots. In yet other embodiments, the microarray comprises from about 1 to about 10,000 spots, about 50 to about 10,000 spots, or about 500 to about 10,000 spots. In some embodiments, the microarray comprises less than about 100,000 spots.

The sample volume which is deposited on each spot and used to form each spot on the microarray can also vary. The volume can depend on diameter of the pin (contact printing), the inherent qualities of the pin hydrophobicity and the method of supplying the sample. In some embodiments, the amount of sample deposited/printed can range from less than about 1 picoliter to about 100 nanoliters.

Samples can be placed or loaded onto the substrate using any one of a number of mechanisms known in the art (see Schena, "*Microarray biochip technology*" Eaton Pub., Natick Mass., 2000, incorporated herein by reference in its entirety). For example, in some embodiments, the samples are printed onto the microarray using a printer. The printing technique can be contact or non-contact printing, and can be automated.

Protein microarray formats can fall into two major classes, the Forward Phase Array (FPA) and the Reverse Phase Array (RPMA), depending on whether the analyte is capture from solution phase or bound to solid substrate. Forward Phase Arrays immobilize a bait molecule, such as a antibody designed to capture a specific analyte within a mixture of test sample proteins. In FPAs, the capture molecule specific for the analyte is immobilized on a substrate. The capture molecule is then exposed to the sample, binding the analyte in the sample and immobilizing the analyte onto the substrate. The bound analyte can then be detected using a detectable label. The label can bind to the analyte directly, or can be attached to a secondary "sandwich" antibody that is specific for the analyte. The capture molecule can be any molecule that has specificity for an analyte and includes, but is not limited to, peptides, proteins, antibodies or fragments thereof, oligomers, DNA, RNA, and PNA. In some embodiments, the capture molecule is an antibody or fragment thereof specific for the analyte.

Reverse Phase Arrays (RPMAs) immobilize the test sample analytes on a solid substrate. In RPMAs, the sample is placed directly on the substrate, allowing analyte in the sample to bind directly to the substrate. A detection molecule specific for the analyte is then exposed to the substrate, allowing an analyte-detection molecule complex to form. The detection molecule can comprise a detectable label to indicate the presence of the analyte. Alternatively, a secondary molecule specific for the detection molecule and comprising a detectable label can be provided, allowing for an analyte-detection molecule-labeled secondary molecule complex to form. RPMAs are highly sensitive and do not require a large amount of sample. The high sensitivity exhibited by RPMAs is due in part to the detection molecule, which can be conjugated to a detectable label, and is also due in part to the fact that the signal from the label can be amplified independently from the immobilized analyte. For example, RPMAs can use tryamide amplification which generates high number of florescent signal on each spot, or florescent signals that are near-IR wavelength, which is outside the emission spectra for nitrocellulose. Amplification chemistries that are available take advantage of methods developed for highly sensitive commercial clinical immunoassays (see, for example, King et al., *J. Pathol.* 183: 237-241 (1997)). Using commercially available automated equipment, RPMAs can also exhibit excellent "within run" and "between run" analytical precision. RPMAs do not require direct labeling of the sample analyte, and do not utilize a two-site antibody sandwich. Therefore, there is no experimental variability introduced due to labeling yield, efficiency or epitope masking.

In a preferred embodiment, RPMA is used to measure the phosphorylated forms of c-erbB2 proteins. The detection molecule and secondary molecule can be any molecule with specificity for c-erbB2 and capture molecule, respectively. Examples of detection and secondary molecules include, but are not limited to, peptides, proteins, antibodies or fragments thereof, oligomers, DNA, RNA, and PNA. In those embodiments in which both a detection molecule and a secondary molecule are present, the detection and secondary molecules can be the same type of molecule, e.g., a protein, or can be different types of molecules, e.g., the detection molecule can be DNA, and the secondary molecule can be an antibody. In some embodiments, both the detection molecule and the secondary molecule are antibodies or fragments thereof.

In some embodiments, the detection or capture molecule, and, if present, the secondary molecule, are both antibodies or fragments thereof. The antibody or fragment thereof that functions as the capture or detection molecule is specific for c-erbB2, in this case, specific for either the activated form of c-erbB2 being measured, or specific for total c-erbB2 protein, regardless of activation state. The antibody or fragment thereof that functions as the secondary molecule, if present, is typically specific for the detection antibody. Antibodies suitable for detecting both activated and total c-erbB2 can be chosen readily by those skilled in the art. See, for example, U.S. patent application Ser. No. 10/798,799, "Combinatorial Therapy for Protein Signaling Diseases," filed Mar. 10, 2004, the entire contents of which is herein incorporated by reference. Suitable antibodies can also be obtained commercially, for example, from Cell Signaling, Inc. (Danvers, Mass.) and BD Biosciences (San Jose, Calif.).

In both FRAs and RPMAs, the capture molecule, the detection antibody, and the secondary molecule, if present, can comprise a detectable label. For example, the capture molecule, the detection molecule, or the secondary molecule, if present, can be conjugated to a detectable label.

Examples of suitable detectable labels include, but are not limited to, fluorescent, radioactive, luminescent and colorimetric labels. Methods and techniques for detecting each type of label are well known in the art.

For fluorescent labels, the labels can have excitation and/or emission spectra in the infrared, near-infrared, visible, or ultra-violet wavelengths. A wide range of fluorescent probes are commercially available (see, e.g., Invitrogen Corporation, Carlsbad, Calif., LI-COR Biosciences, Lincoln Nebr.). Examples of suitable fluorescent probes include, but are not limited to, phycoerythrin or other phycobilliproteins such as allophycocyanin, lanthanide-based dyes, and phthalocyanine dyes. In addition, methods and reagents for coupling fluorescent probes to proteins, including antibodies, are well known in the art (see, for example, technical handbooks from Invitrogen Corporation (Carlsbad, Calif.) and Pierce (Thermo Fisher Scientific, Inc., Rockford, Ill.).

Suitable radioactive labels include those containing the isotopes $C^{14}$, $P^{32}$, and $S^{35}$. Examples of suitable luminescent labels include quantum dots, 1,2-Dioxetanes, and luminal. Examples of suitable colorimetric labels include DAB. Methods for using each of these labels and their corresponding detection systems are known to the artisan skilled in the art.

In some embodiments, the signal from the detectable label can be amplified. Amplification is helpful for achieving sensitivity adequate for analysis of relatively low abundance proteins. Amplification of the label signal can be achieved by enzymatic cleavage of colorimetric, luminescent or fluorescent substrates, by utilizing avidin/biotin signal amplification systems known in the art, or by taking advantage of the polymerase chain reaction by coupling nucleic acids to protein for detection. For example, amplification chemistries can take advantage of methods developed for highly sensitive commercial clinical immunoassays. See, for example, King et al., *J. Pathol.* 183:237-241 (1997). Coupling the capture molecule with highly sensitive tyramide-based avidin/biotin signal amplification systems can also yield detection sensitivities down to fewer than 1,000-5,000 molecules/spot. In a particular embodiment, a biopsy of 10,000 cells can yield 100 RPMA microarrays, and each array can be probed with a different antibody.

The measurements obtained for activated c-erbB2 in each sample can be "normalized" to total protein in the sample using methods known in the art, such that the detected level of phosphorylated c-erbB2 protein is independent of the amount or concentration of the sample spotted on the array. For example, each lysate is measured for phosphorylated c-erbB2 as well as total protein as measured by SYPRO Ruby Red protein stain (Molecular Probes, Eugene Oreg.), obtained by staining a different slide with the total protein stain.

Significantly elevated levels of activated c-erbB2, e.g., the level of phosphorylated c-erbB2 over baseline values, are those that are statistically significant Cut-points for "activation" status are determined by comparing the level of phosphorylated c-erbB2 measured by reverse phase protein array analysis of sample tumor epithelial cells micro-dissected from a patient to reference standards.

The reference standards are a series of lysates derived from the breast cancer cell line SKBR3 and the carcinoma cell line MDA175. Prior to lysis, the cells are stimulated with EGF producing a reference standard with high (SKBR3) and low (MDA175) amounts of phosphorylated c-erbB2. In the alternative, the reference standards are a series of lysates derived from a c-erbB2-negative cell line spiked with recombinant or partially purified phosphorylated c-erbB2, or spiked with phosphorylated c-erbB2 peptide at a series of known concentrations of phosphorylated c-erbB2.

In a subject with a cancer of epithelial origin who has been determined to be c-erbB2 negative by immunohistochemistry (IHC) and by fluorescence in situ hybridization (FISH), a level of phosphorylation greater than the cut-point in one or more diseased cells indicates that the subject has a high level of phosphorylated c-erbB2 receptor and should be included in c-erbB2-directed treatment and therapy. In a subject with a cancer of epithelial origin, a level of phosphorylation greater than the cut-point value in one or more diseased cells indicates that the subject has a poor prognosis and would benefit from treatment with an EGF receptor dimerization inhibitor, trastuzumab or an analogue compound thereof, or a c-erbB2 kinase inhibitor. In the alternative, in a subject with a cancer of epithelial origin who has been determined to be c-erbB2 positive by IHC and by FISH, a level of phosphorylation smaller than the cut-point value in one or more diseased cells indicates that the subject should be excluded from treatment with an EGF receptor dimerization inhibitor, trastuzumab or an analogue compound thereof, or a c-erbB2 kinase inhibitor.

Thus, the present invention provides reliable methods to determine whether a subject with a cancer of epithelial origin who has been determined to be c-erbB2 negative by IHC and by FISH should be selected and included for c-erbB2-directed treatment and therapy. Further, the invention provides reliable methods to identify a subject with a cancer of epithelial origin who would benefit from treatment with an EGF receptor dimerization inhibitor, trastuzumab or an analogue compound thereof, or a c-erbB2 kinase inhibitor; determine a priori a poor or a good prognosis for a subject with a cancer of epithelial origin; and determine the level of phosphorylation of the c-erbB2 receptor in a subject with a cancer of epithelial origin. Further, the present invention provides a reliable method to determine whether a subject with a cancer of epithelial origin who has been determined to be c-erbB2 positive by IHC and by FISH should be excluded from treatment with an EGF dimerization inhibitor, trastuzumab or an analogue compound thereof, or a c-erbB2 kinase inhibitor.

In particular, the present invention provides reliable methods to identify subsets of subjects with a cancer of epithelial origin characterized by a high level of phosphorylated c-erbB2 which does not correlate with the over-expression of total c-erbB2, as measured by FISH or IHC. These subsets of subjects remains typically undetected when using IHC and FISH methods of analysis for the over-expression of c-erbB2/HER2, and thus are automatically excluded from c-erbB2-direct therapy, despite the fact that these subjects would positively respond to therapy with an EGF dimerization inhibitor, trastuzumab or an analogue compound thereof, or a c-erbB2 kinase inhibitor. Providing a net improvement over the IHC and FISH methodologies, the method of the present invention relies on the measurement of phosphorylated c-erbB2 as a predictive marker of pathologic complete response and survival in subjects with a cancer of epithelial origin and allows identification and inclusion of subsets of subjects with a high level of phosphorylated c-erbB2 for treatment and therapy with an EGF dimerization inhibitor, trastuzumab or an analogue compound thereof, or a c-erbB2 kinase inhibitor.

Furthermore, the present invention provides a reliable method to determine whether a subject with a cancer of epithelial origin who has been determined to be c-erbB2 positive by immunohistochemistry (IHC) and by fluorescence in situ hybridization (FISH) should be excluded from treatment with an EGF dimerization inhibitor, trastuzumab or an analogue compound thereof, or a c-erbB2 kinase inhibitor because of a non-significant level of phosphorylated c-erbB2 in epithelial tumor tissue.

Cancers of epithelial origin include, but are not limited to, glioblastoma, adenocarcinoma, cancer of the prostate, lung, breast, ovary, stomach, pancreas, bladder, colon, rectum, kidney, head, neck or any combination thereof.

Dosages and modes of administration of the EGF receptor dimerization inhibitor, trastuzumab or an analogue compound thereof, or a c-erbB2 kinase inhibitor are well known to those of skill in the art, e.g., medical practitioners or clinicians.

Analogues of trastuzumab include, but are not limited to, monoclonal antibodies, fragments and variants thereof that bind the HER2/neu receptor and inhibit HER2/neu receptor dimerization. Trastuzumab or an analogue compound thereof may be administered as adjuvant therapy to a subject that is being treated with a conventional anti-tumor drug including, but not limited to, paclitaxel, doxorubicin, cyclophosphamide, a COX-2 inhibitor, a non-voltage gated calcium influx channel effector and an EGF kinase inhibitor.

C-erbB2 kinase inhibitors include, but are not limited to, lapatinib and analogue compounds in the same class of lapatinib, such as GW2974 and GW2016. Lapatinib and analogue compounds thereof may be administered to a subject that is being treated with capecitabine. Dosages and modes of administration for these additional treatments are known to those of skill in the art. Such additional anti-cancer treatments or therapies can be administered concurrently with, or sequentially with, treatment with an EGF receptor dimerization inhibitor, trastuzumab or a c-erbB2 kinase inhibitor.

The following examples are illustrative only and do not limit the scope of the invention in any way.

EXAMPLES

Example 1

A study set of 127 laser capture micro-dissected (LCM) breast cancer specimens were analyzed for total and phosphorylated levels of c-erbB2/HER2 using reverse phase protein microarray (RPMA) technology, as described in Sheehan et al., MCP 2005 and Sheehan et al., Oncogene, 2007. For each patient, approximately 20,000 pure populations of tumor epithelial cells were obtained by laser capture microdissection. Over expression of HER2 is measured using FISH to compare the copy number of HER2 to a single copy reference, CEP17. See, e.g., Stevens et al, *J. Mol. Diagn.* (2007) 9:144-150, which is incorporated herein by reference. Phosphorylation of HER2 is measured using an antibody that is specific for phosphorylated HER2.

The results of analysis of correlation of phosphorylated c-erbB2/HER2 with total c-erbB2 as measured by IHC are presented in FIG. 1 as a graph comparing the phosphorylation level of c-erbB2 of laser capture micro-dissected breast tumor epithelium as measured by reverse phase protein microarray analysis (RPMA) (y-axis). RPMA values are expressed in relative intensity units. The x-axis is the sample number, with the samples plotted in order, from left to right, of increasing phosphorylated c-erbB2 relative intensity values from the RPMA analysis. The squares represent a subpopulation of HER2-negative subjects with a negative IHC staining of 1+; the circles represent a subpopulation of subjects with an intermediate IHC staining of 2+; and the triangles represent a subpopulation of HER2-positive subjects with a positive IHC staining of 3+. While the RPMA results indicated excellent correlation of phospho HER2 with IHC, a significant minority of patients presented phosphorylated c-erbB2 levels that were unexpectedly higher or lower compared to the total levels of c-erbB2.

FIG. 2 presents a graph comparing the phosphorylation level of c-erbB2 of laser capture micro-dissected breast tumor epithelium as measured by reverse phase protein microarray analysis (RPMA) (y-axis) to the total level of c-erbB2 as measured by IHC and FISH (x-axis). RPMA values are expressed in relative intensity units. The red squares represent a subpopulation of HER2-negative subjects with a negative IHC staining of 1+; the yellow circles represent a subpopulation of subjects with an intermediate IHC staining of 2+; and the green triangles represent a subpopulation of HER2-positive subjects with a positive IHC staining of 3+. The bottom right circle indicates measurements from 5 subjects (5 of 20, 25% IHC+) that were determined both by IHC and FISH to be HER2-positive, but resulted phospho-c-erbB2-negative by RPMA and presented the same level of phosphorylated c-erbB2 presented by the majority of the HER2-negative subjects (25% of the HER2-positive population). The top left circle indicates a subpopulation of seven HER2-negative subjects, as determined by both IHC and FISH, that nevertheless were determined unexpectedly to be phospho HER2-positive subjects (16% of the HER2-negative population). All HER2-positive patients were treated with trastuzumab. This subset of subjects was not identified when the total levels of c-erbB2 were measured by IHC or FISH, indicating that this population has a distinct phenotype characterized by a low level of total c-erbB2 protein and a high level of phosphorylated c-erbB2 receptor. These results clearly demonstrate that response to c-erbB2-direct therapy is best measured by phosphorylated c-erbB2, and not by the total levels of the protein. Identification of patients in both types of cohorts is likely to dramatically increase the response rate to c-erbB2 targeted therapy.

Example 2

The signaling profiles of tumors from FISH−/IHC− phosphoHER2+ (FISH−/pHER2+) breast cancer population were analyzed for receptor heterodimerization and downstream signaling activation and compared to that of the FISH+/IHC+ phosphoHER2+ (FISH+/pHER2+) population. If the HER2 protein is indeed activated/phosphorylated in FISH−/IHC− populations, then evidence for productive signal transduction should be found in the heterodimerization with other members of the EGFR family and activation of downstream pathway substrates such as AKT and SHC.

Figure 3A:
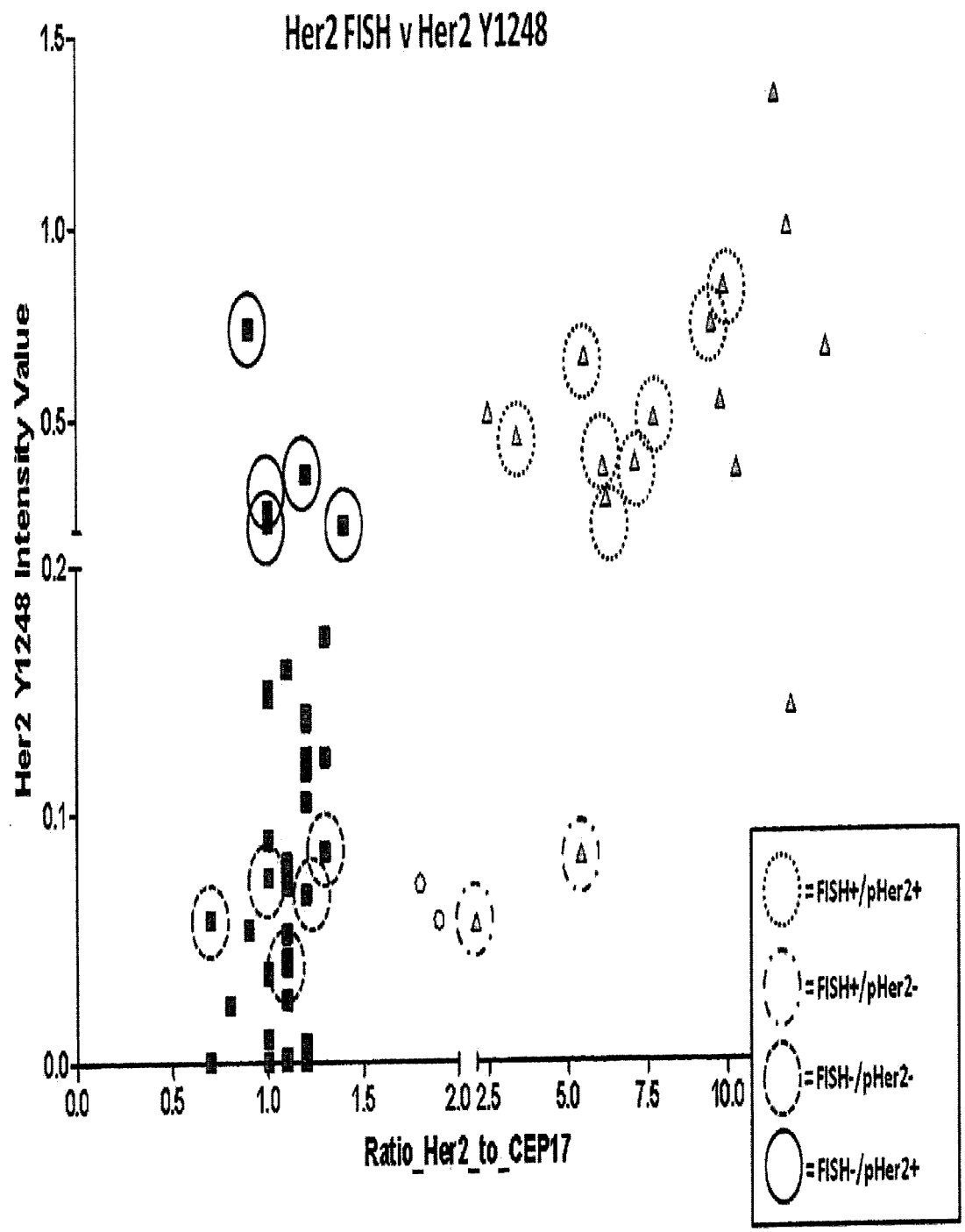
FIGS. 3A-B present data comparing the signaling profile of tumors from FISH−/IHC− phosphoHER2+ breast cancers with those of FISH+/IHC+ phosphor-cerbB2+ breast cancers. Panel A compares the HER2 phosphorylation of tumors that are FISH+/IHC+ or FISH−/IHC−. Panel B compares the EGFR phosphorylation (Y992) of tumors that are FISH+/IHC+ or FISH−/IHC−.

Using techniques as described above, the HER2 phosphorylation states of five FISH−/pHER2+ tumors were compared with that of FISH+/pHER2+ tumors, FISH+/pHER2− tumors and FISH−/pHER2− tumors. As shown in FIG. 3A, the FISH−/pHER2+ population had similar phosphorylation levels as the FISH+/pHER2+ population, which was significantly higher than the pHER2− populations.

Figure 3B:
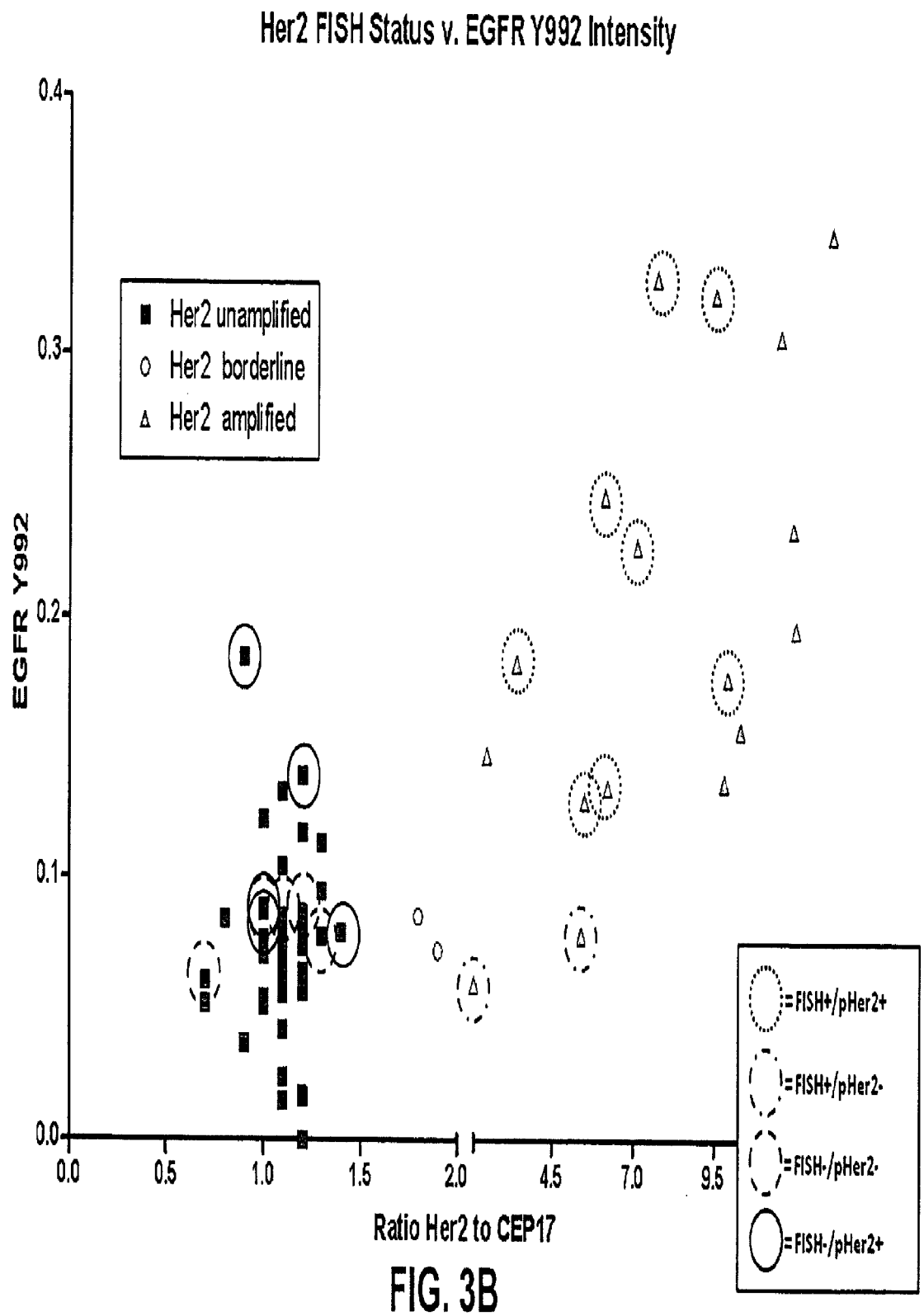
Figure 4:
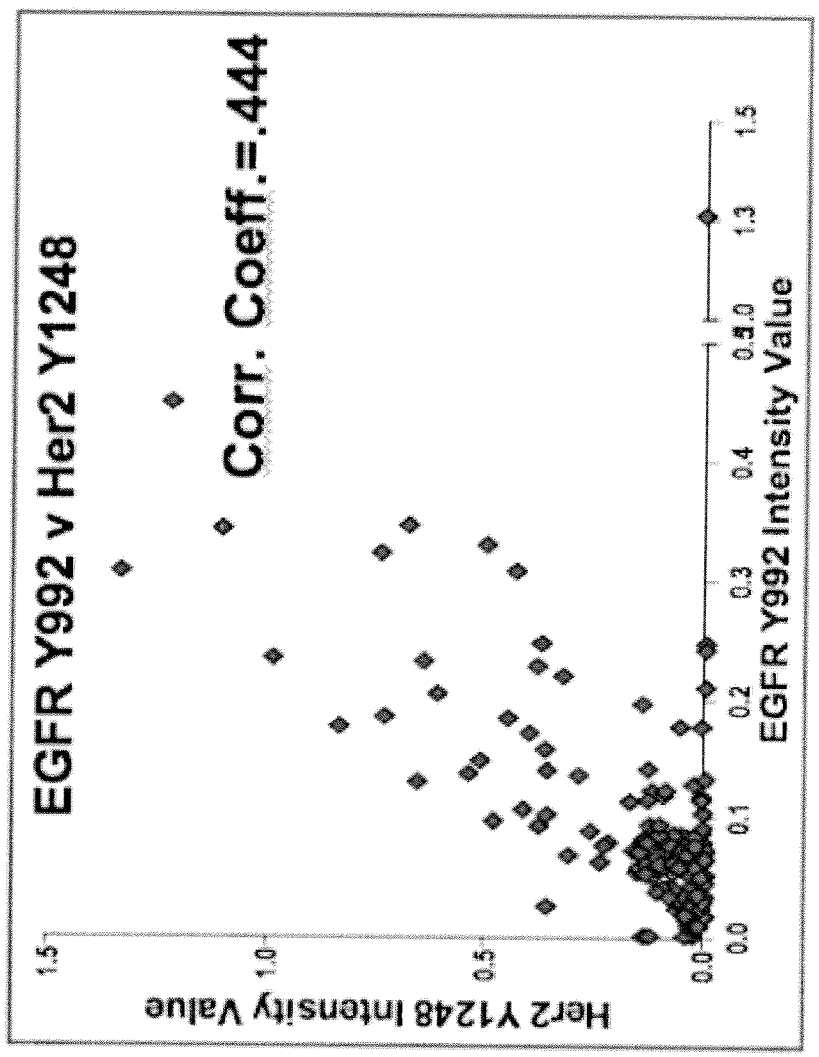
FIG. 4 shows the correlation between EGFR phosphorylation (Y992) and HER2 phosphorylation in tumors.

Likewise, the EGFR phosphorylation status of these tumor populations were compared. As shown in FIG. 3B, the highest levels of pHER2 correlated with the highest levels of pEGFR, as measured using an antibody specific for phosphorylated EGFR,Y992. These data strongly suggest receptor heterodimerization, which is further confirmed in FIG. 4, which shows that EGFR phosphorylation and HER2 phosphorylation are highly concordant, with a correlation coefficient of 0.444.

Figure 5:
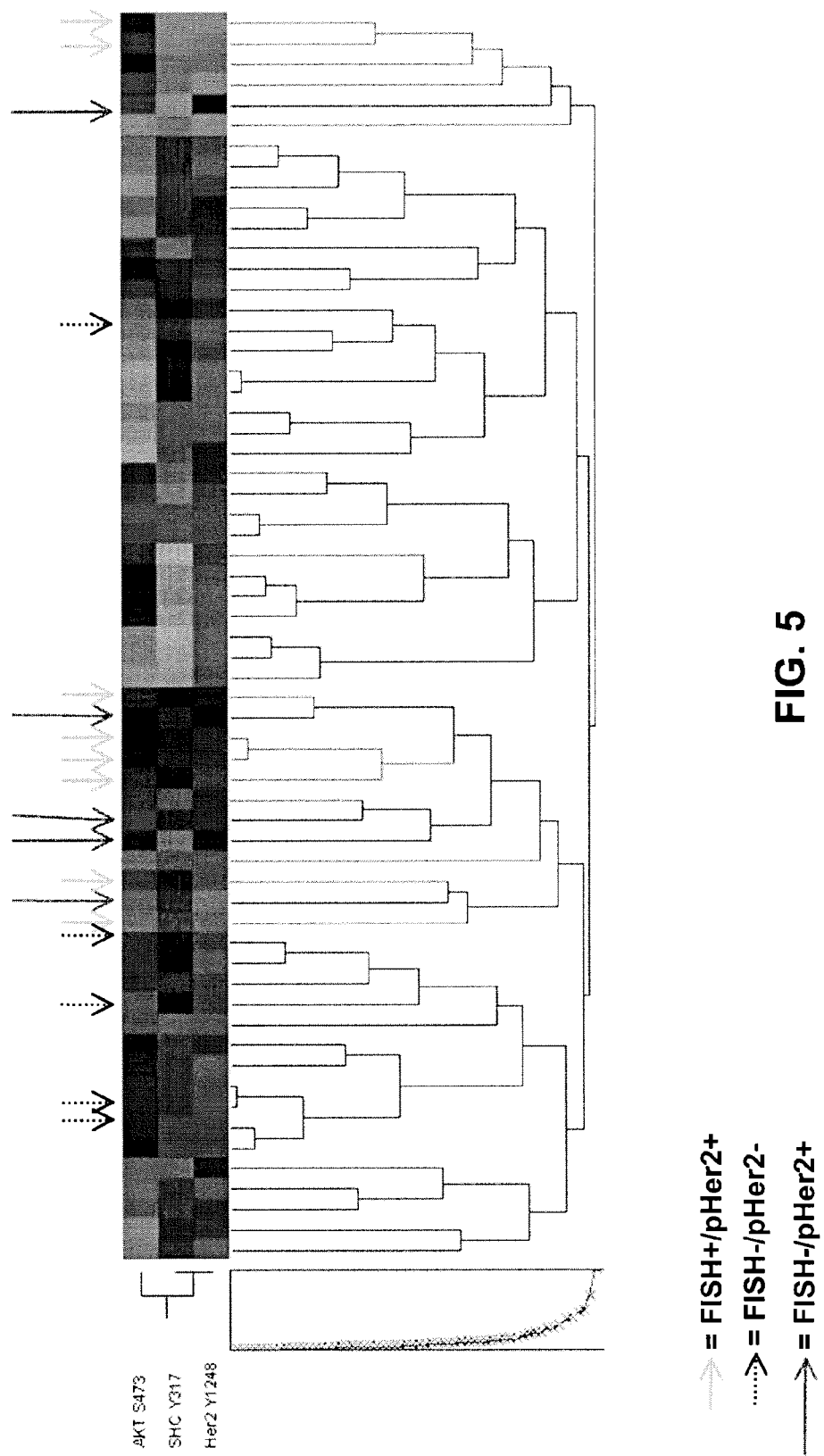
FIG. 5 presents the unsupervised clustering analysis of HER2 signaling and downstream AKT and SHC in tumors with differing FISH/IHC and phosphoHER2 status.
Figure 6A:
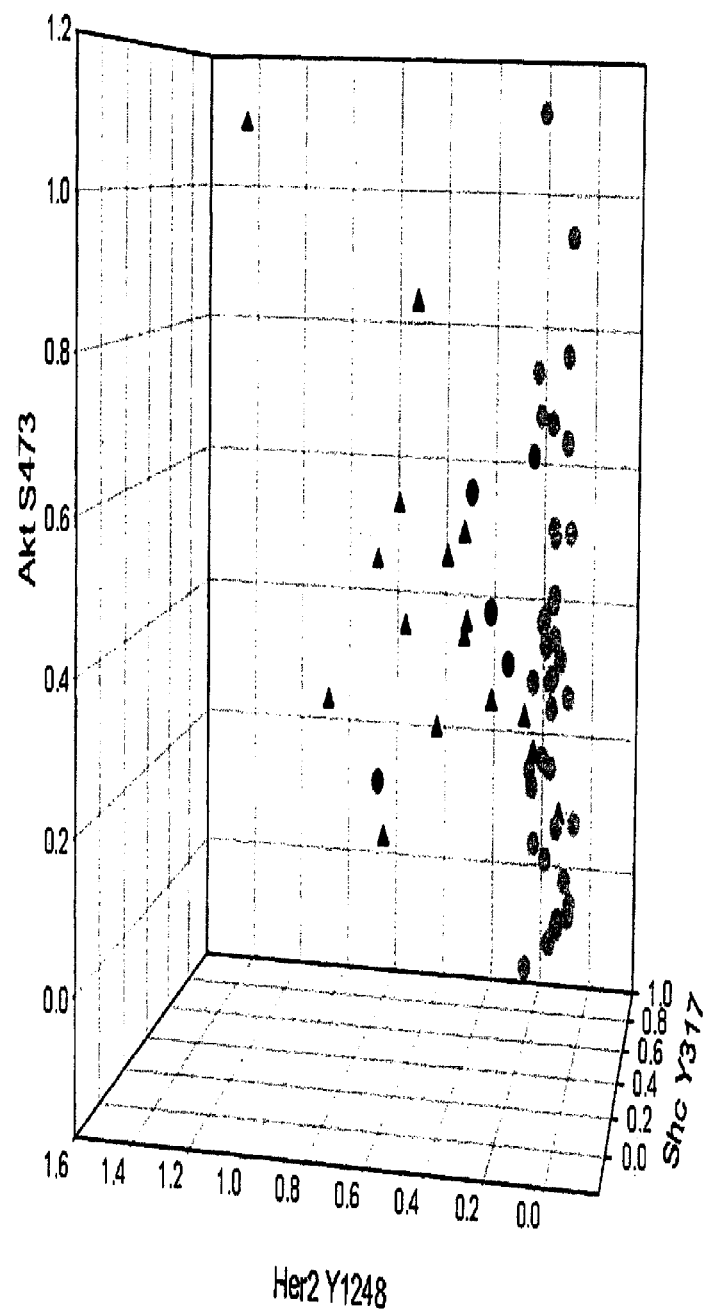
FIGS. 6A-C are three way scatter plots of phosphorHer2 (pHER2), phosphoAKT (pAKT) and phosphoSHC (pSHC) in FISH−/pHER2− (grey circles), FISH−/pHER2+ (black circle) and FISH+/pHER2+ (black triangle) tumors. All axis are relative intensity values of each of the phospho-endpoint measured.
Figure 6B:
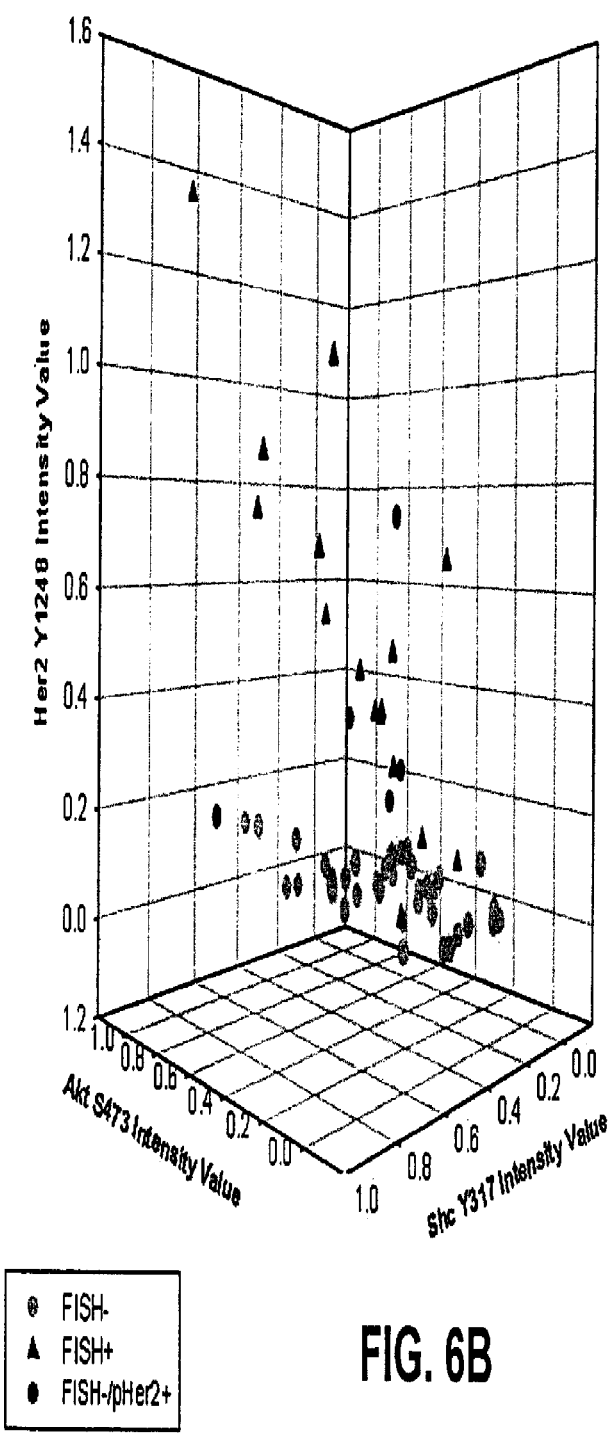
Figure 6C:
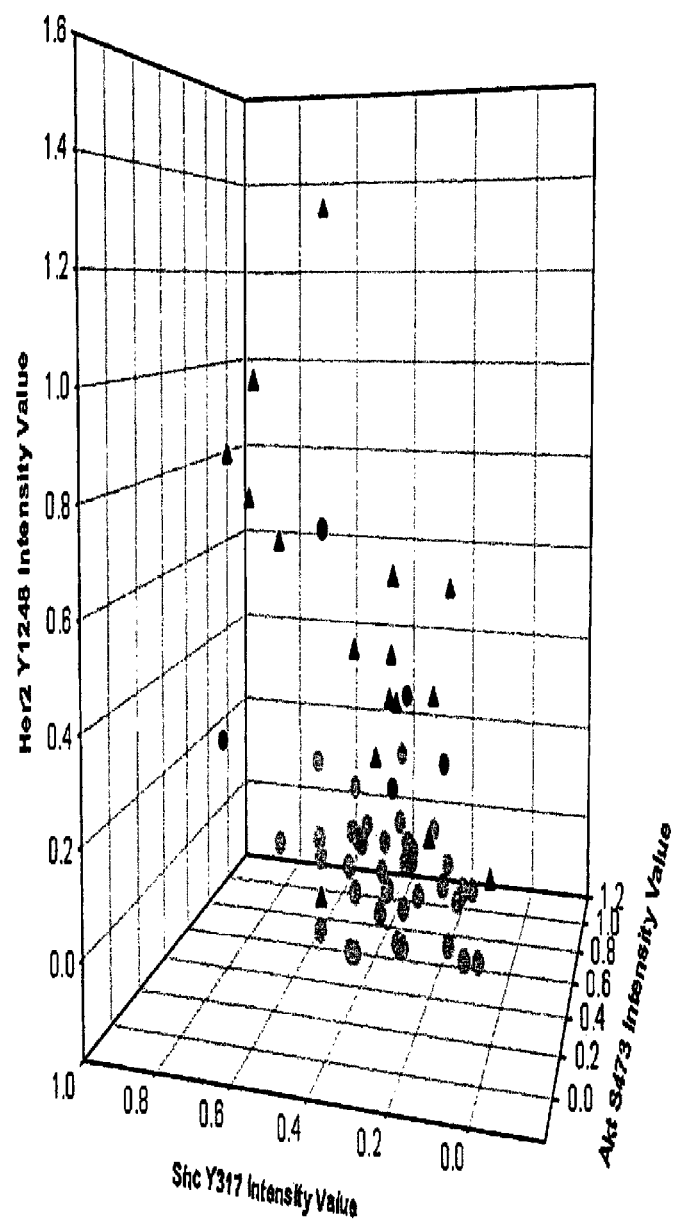

To evaluate the downstream activation of HER2 signaling in the FISH−/pHER2+ tumors, the phosphorylation of two known downstream kinases in the HER2/EGFR signaling network, AKT (protein kinase B) and SHC were measured. Responsiveness to HERCEPTIN® has been reported to be coincident with activation of AKT and SHC (Junttila et al, *Cancer Cell.* (2009) 15:429-440; Zhou et al. *Clin. Cancer Res.* (2004) 10:6779-6788). As shown in FIG. 5, unsupervised clustering analysis (described in Wulfkuhle et al, *J. Proteome Res.* (2008) 7:1508-1517) reveals that FISH−/pHER2+ tumors display activation of AKT and SHC. This activation strongly suggests that the HER2 phosphorylation observed in the FISH−/pHER2+ tumors produce functional pathway activation. This same activation is also presented in FIG. 6 as a three way clustering plot in which the FISH−/pHER2+ cohort cluster together with the FISH+/pHER2+ cohort and is distinct from the FISH−/pHER2− cohort.

Taken together, the foregoing data provide evidence that FISH−/pHER2+ tumors have functional HER2-driven pathway signaling consistent with that of FISH+/pHER2+ tumors. Further, this functional signaling is associated with and likely caused by the phosphorylation of HER2. This functional signaling is productive and may represent a new cohort of tumors that are responsive to HERCEPTIN® presently overlooked by current HER2 testing methods.

All publications cited in this specification are herein incorporated by reference in their entirety to the same extent as if each individual document was specifically and individually indicated to be incorporated by reference in its entirety. While the invention has been described with reference to a particularly preferred embodiment, it will be appreciated that modifications can be made without departing from the spirit of the invention. Such modifications are intended to fall within the scope of the appended claims.

What is claimed is:

1. A method for treating a human with a cancer of epithelial origin, who has been determined to be c-erbB2 negative by immunohistochemistry (IHC) or by fluorescence in situ hybridization (FISH), comprising administering an erbB2-directed treatment and therapy to the human, if the human has been identified for such treatment by a method comprising (a) measuring the level of phosphorylation of the c-erbB2 receptor in one or more diseased cells obtained from the cancerous epithelial tissue of the human using a quantitative immunoassay; (b) comparing the level of phosphorylation of the receptor in the one or more diseased cells to the level of phosphorylation of the receptor in one or more reference standards having a known phosphorylation level; and (c) determining that the human should be treated with erbB2-directed treatment and therapy if the level of phosphorylation of the receptor in the one or more diseased cells is greater than the cutpoint value obtained by comparing a population average level of phosphorylation of the receptor in known erbB2-phosphorylated cancers to the level of phosphorylation of the receptor in the reference standards.

2. The method of claim 1, wherein the erbB2-directed treatment and therapy comprises administering an EGF receptor dimerization inhibitor to the human.

3. The method of claim 1, wherein the erbB2-directed treatment and therapy comprises administering trastuzumab or an analogue compound thereof to the human.

4. The method of claim 1, wherein the erbB2-directed treatment and therapy comprises administering trastuzumab to the human.

5. The method of claim 1, wherein the erbB2-directed treatment and therapy comprises administering a c-erbB2 kinase inhibitor to the human.

6. The method of claim 1, wherein the erbB2-directed treatment and therapy comprises administering lapatinib or an analogue compound thereof to the human.

7. The method of claim 1, wherein the erbB2-directed treatment and therapy comprises administering lapatinib to the human.

8. The method of claim 1, wherein the cancer of epithelial origin is breast cancer.

9. The method of claim 8, wherein the one or more diseased cells are obtained by micro-dissecting the cells from the breast cancer tissue of the human and the level of phosphorylation of the c-erbB2 receptor in the one or more diseased cells is measured by protein microarray analysis.

10. The method of claim 8, wherein the erbB2-directed treatment and therapy comprises administering trastuzumab to the human.

11. The method of claim 1, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

12. The method of claim 1, wherein the cancer of epithelial origin is a cancer of the breast, lung, prostate, colon, rectum, pancreas, or ovary.

13. The method of claim 1, wherein the cancer of epithelial origin is a cancer of the breast, lung, prostate, colon or rectum.

14. A method for treating a human with a cancer of epithelial origin, who has been determined to be c-erbB2 negative by immunohistochemistry (IHC) or by fluorescence in situ hybridization (FISH), comprising administering an erbB2-directed treatment and therapy to the human, if the human has been identified for such treatment by a method comprising (a) using an assay to measure the level of phosphorylation of the c-erbB2 receptor in one or more diseased cells obtained from the cancerous epithelial tissue of the human; (b) comparing the level of phosphorylation of the receptor in the one or more diseased cells to the level of phosphorylation of the receptor in one or more reference standards having a known phosphorylation level; and (c) determining that the human should be treated with erbB2-directed treatment and therapy if the level of phosphorylation of the receptor in the one or more diseased cells is greater than the cut-point value obtained by comparing a population average level of phosphorylation of the receptor in known erbB2-phosphorylated cancers to the level of phosphorylation of the receptor in the reference standards.

15. The method of claim 14, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

16. The method of claim 14, wherein the cancer of epithelial origin is a cancer of the breast, lung, prostate, colon, rectum, pancreas, or ovary.

17. The method of claim 14, wherein the cancer of epithelial origin is a cancer of the breast, lung, prostate, colon or rectum.

18. The method of claim 14, wherein the cancer of epithelial origin is breast cancer.

19. A method for identifying a human with a cancer of epithelial origin, who has been determined to be c-erbB2 negative by immunohistochemistry (IHC) or by fluorescence in situ hybridization (FISH), who would benefit from erbB2-directed treatment and therapy, comprising (a) measuring the level of phosphorylation of the c-erbB2 receptor in one or more diseased cells obtained from the cancerous epithelial tissue of the human by protein microarray analysis; (b) comparing the level of phosphorylation of the receptor in the one or more diseased cells to the level of phosphorylation of the receptor in one or more reference standards having a known phosphorylation level; and (c) determining that the human should be treated with erbB2-directed treatment and therapy if the level of phosphorylation of the receptor in the one or more diseased cells is greater than the cut-point value obtained by comparing a population average level of phosphorylation of the receptor in known erbB2-phosphorylated cancers to the level of phosphorylation of the receptor in the reference standards.

20. The method of claim 19, wherein the one or more diseased cells are obtained by micro-dissecting the cells from the cancerous epithelial tissue of the human.

21. The method of claim 20, wherein the micro-dissecting comprises laser capture micro-dissection.

22. The method of claim 21, wherein the protein microarray analysis comprises reverse phase protein microarray analysis.

23. The method of claim 19, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

24. The method of claim 19, wherein the cancer of epithelial origin has metastasized to at least one organ site distinct from the originating organ.

25. The method of claim 19, wherein the cancer of epithelial origin is a cancer of the breast, lung, prostate, colon, or rectum.

26. The method of claim 19, wherein the cancer of epithelial origin is breast cancer.

27. The method of claim 19, wherein the cancer of epithelial origin is a cancer of the breast, lung, prostate, colon, rectum, pancreas or ovary.

28. The method of claim 26, wherein the protein microarray analysis comprises reverse phase protein microarray analysis.

29. The method of claim 28, wherein the one or more diseased cells are obtained by micro-dissecting the cells from the cancerous epithelial tissue of the human.

30. A method for identifying a human with a cancer of epithelial origin, who has been determined to be c-erbB2 positive by immunohistochemistry (IHC) or by fluorescence in situ hybridization (FISH), who should be excluded from treatment with an EGF receptor dimerization inhibitor, trastuzumab or an analogue compound thereof, or a c-erbB2 kinase inhibitor, comprising (a) measuring the level of phosphorylation of the c-erbB2 receptor in one or more diseased cells obtained from the cancerous epithelial tissue of the human by protein microarray analysis; (b) comparing the level of phosphorylation of the receptor in the one or more diseased cells to the level of phosphorylation of the receptor in one or more reference standards having a known phosphorylation level; and (c) determining that the human should be excluded from treatment with an EGF receptor dimerization inhibitor, trastuzumab or an analogue compound thereof, or a c-erbB2 kinase inhibitor if the level of phosphorylation of the receptor in the one or more diseased cells is smaller than the cut-point value obtained by comparing a population average level of phosphorylation of the receptor in known erbB2-phosphorylated cancers to the level of phosphorylation of the receptor in the reference standards.

31. The method of claim 30, wherein the one or more diseased cells are obtained by micro-dissecting the cells from the cancerous epithelial tissue of the human.

32. The method of claim 31, wherein the micro-dissecting comprises laser capture micro-dissection.

33. The method of claim 32, wherein the protein microarray analysis comprises reverse phase protein microarray analysis.

34. The method of claim 30, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

35. The method of claim 30, wherein the cancer of epithelial origin is a cancer of the breast, lung, prostate, colon, or rectum.

36. The method of claim 30, wherein the cancer of epithelial origin is breast cancer.

37. The method of claim 30, wherein the cancer of epithelial origin is a cancer of the breast, lung, prostate, colon, rectum, pancreas or ovary.

38. The method of claim 30, wherein the cancer of epithelial origin has metastasized to at least one organ site distinct from the originating organ.

39. A method of using a protein microarray for identifying a human with a cancer of epithelial origin, who has been determined to be c-erbB2 negative by immunohistochemistry (IHC) or by fluorescence in situ hybridization (FISH), who would benefit from erbB2-directed treatment and therapy, comprising (a) using the protein microarray to measure the level of phosphorylation of the c-erbB2 receptor in one or more diseased cells obtained from the cancerous epithelial tissue of the human; (b) comparing the level of phosphorylation of the receptor in the one or more diseased cells to the level of phosphorylation of the receptor in one or more reference standards having a known phosphorylation level; and (c) determining that the human should be treated with erbB2-directed treatment and therapy if the level of phosphorylation of the receptor in the one or more diseased cells is greater than the cut-point value obtained by comparing a population average level of phosphorylation of the receptor in known erbB2-phosphorylated cancers to the level of phosphorylation of the receptor in the reference standards.

40. The method of claim 39, wherein the protein microarray comprises a reverse phase protein microarray.

41. The method of claim 39, wherein the cancer of epithelial origin is a cancer of the breast, lung, prostate, colon, or rectum.

42. The method of claim 39, wherein the cancer of epithelial origin is breast cancer.

43. The method of claim 39, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

44. The method of claim 39, wherein the cancer of epithelial origin is a cancer of the breast, lung, prostate, colon, rectum, pancreas, or ovary.

45. A method of using a protein microarray for identifying a human with a cancer of epithelial origin, who has been determined to be c-erbB2 positive by immunohistochemistry (IHC) or by fluorescence in situ hybridization (FISH), who should be excluded from treatment with an EGF receptor dimerization inhibitor, trastuzumab or an analogue compound thereof, or a c-erbB2 kinase inhibitor, comprising (a) using the protein microarray to measure the level of phosphorylation of the c-erbB2 receptor in one or more diseased cells obtained from the cancerous epithelial tissue of the human; (b) comparing the level of phosphorylation of the receptor in the one or more diseased cells to the level of phosphorylation of the receptor in one or more reference standards having a known phosphorylation level; and (c) determining that the human should be excluded from treatment with an EGF receptor dimerization inhibitor, trastuzumab or an analogue compound thereof, or a c-erbB2 kinase inhibitor if the level of phosphorylation of the receptor in the one or more diseased cells is smaller than the cut-point value obtained by comparing a population average level of phosphorylation of the receptor in known erbB2-phosphorylated cancers to the level of phosphorylation of the receptor in the reference standards.

46. The method of claim 45, wherein the cancer of epithelial origin is adenocarcinoma or is a cancer of the breast, prostate, esophagus, liver, skin, lung, ovary, stomach, pancreas, bladder, colon, rectum, kidney, head, neck or any combination thereof.

47. The method of claim 45, wherein the cancer of epithelial origin is a cancer of the breast, lung, prostate, colon, rectum, pancreas, or ovary.

48. The method of claim 45, wherein the cancer of epithelial origin is a cancer of the breast, lung, prostate, colon or rectum.

49. The method of claim 45, wherein the cancer of epithelial origin is breast cancer.

\* \* \* \* \*